(12) United States Patent
Takino et al.

(10) Patent No.: US 10,085,895 B2
(45) Date of Patent: Oct. 2, 2018

(54) DISPOSABLE DIAPER

(71) Applicant: Unicharm Corporation, Shikokuchuo-shi, Ehime (JP)

(72) Inventors: Shunsuke Takino, Kanonji (JP); Hideaki Maki, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 15/319,366

(22) PCT Filed: Jul. 22, 2015

(86) PCT No.: PCT/JP2015/070801
§ 371 (c)(1),
(2) Date: Dec. 15, 2016

(87) PCT Pub. No.: WO2016/051936
PCT Pub. Date: Apr. 7, 2016

(65) Prior Publication Data
US 2017/0128281 A1 May 11, 2017

(30) Foreign Application Priority Data

Sep. 30, 2014 (JP) .................................. 2014-202488

(51) Int. Cl.
*A61F 13/495* (2006.01)
*A61F 13/494* (2006.01)
(Continued)

(52) U.S. Cl.
CPC .. *A61F 13/49406* (2013.01); *A61F 13/49001* (2013.01); *A61F 13/495* (2013.01);
(Continued)

(58) Field of Classification Search
CPC .......... A61F 13/49001; A61F 13/49466; A61F 2013/49493
(Continued)

(56) References Cited

U.S. PATENT DOCUMENTS 2,749,558 A * 6/1956 Constantin .............. A61F 5/451
4/144.3
3,395,708 A * 8/1968 Hervey ................. A61F 13/505
162/179
(Continued)

FOREIGN PATENT DOCUMENTS

CA 2146065 * 10/1996
JP 09-070414 A 3/1997
(Continued)

OTHER PUBLICATIONS

International Search Report for PCT/JP2015/070801 dated Oct. 20, 2015.
(Continued)

*Primary Examiner* — Paula L Craig
(74) *Attorney, Agent, or Firm* — Hauptman Ham, LLP

(57) ABSTRACT

In a disposable diaper, a back waist region includes a belt region extending in a transverse direction on a skin-facing surface and a downward openable pocket facing, in a front-back direction, a central sub-region in the transverse direction of the belt region. The pocket is defined by a pocket outside wall facing the middle portion in the front-back direction and extending upward from the crotch region, a pocket inside wall facing the pocket outside wall and the belt region, respectively, in the front-back direction, and being continuous with the pocket outside wall through a folded portion and extending downward from the fold line so as to become continuous with the pocket inside wall of the middle portion in the belt region, and both pocket lateral portions formed from the respective lateral portions of the (Continued)

inside and outside walls, and tucked inward in the transverse direction.

12 Claims, 11 Drawing Sheets

(51) Int. Cl.
  *A61F 13/496*   (2006.01)
  *A61F 13/49*   (2006.01)
  *A61F 13/53*   (2006.01)
(52) U.S. Cl.
  CPC ...... *A61F 13/496* (2013.01); *A61F 13/49012* (2013.01); *A61F 13/53* (2013.01)
(58) Field of Classification Search
  USPC .............................. 604/348, 385.19, 385.201
  See application file for complete search history.

(56) References Cited

U.S. PATENT DOCUMENTS

| | | | | |
|---|---|---|---|---|
| 3,559,648 A * | 2/1971 | Mason, Jr. | ............ | A61F 13/493 604/365 |
| 3,577,989 A * | 5/1971 | Anderson | ............ | A61F 5/4401 604/348 |
| 3,604,423 A * | 9/1971 | Fraser | ............ | A61F 13/56 604/385.13 |
| 3,995,640 A * | 12/1976 | Schaar | ............ | A61F 13/49001 604/378 |
| 4,085,753 A * | 4/1978 | Gellert | ............ | A61F 13/551 604/365 |
| 4,738,677 A * | 4/1988 | Foreman | ............ | A61F 5/4401 604/378 |
| 4,753,646 A * | 6/1988 | Enloe | ............ | A61F 13/49466 604/378 |
| 5,019,070 A * | 5/1991 | Ruben | ............ | A61F 13/49004 604/379 |
| 5,062,840 A * | 11/1991 | Holt | ............ | A61F 13/495 604/385.19 |
| 5,069,672 A * | 12/1991 | Wippler | ............ | A61F 13/62 604/385.14 |
| 5,071,414 A * | 12/1991 | Elliott | ............ | A61F 13/551 604/358 |
| 5,106,385 A * | 4/1992 | Allen | ............ | A61F 13/493 604/385.21 |
| 5,397,318 A * | 3/1995 | Dreier | ............ | A61F 13/49009 604/385.19 |
| 5,462,541 A * | 10/1995 | Bruemmer | ............ | A61F 13/49009 604/378 |
| 5,569,229 A * | 10/1996 | Rogers | ............ | A61F 13/42 604/358 |
| 5,576,090 A * | 11/1996 | Suzuki | ............ | A61F 13/15593 156/164 |
| 5,593,401 A * | 1/1997 | Sosalla | ............ | A61F 13/49011 604/385.28 |
| 5,667,503 A * | 9/1997 | Roe | ............ | A61F 13/495 604/385.19 |
| 5,690,627 A * | 11/1997 | Clear | ............ | A61F 13/15593 604/385.29 |
| 5,817,086 A * | 10/1998 | Kling | ............ | A61F 13/495 604/385.19 |
| 5,843,065 A * | 12/1998 | Wyant | ............ | A61F 13/4915 604/385.09 |
| 5,904,675 A * | 5/1999 | Laux | ............ | A61F 13/49011 604/385.29 |
| 5,938,652 A * | 8/1999 | Sauer | ............ | A61F 13/49011 604/385.29 |
| 6,102,899 A * | 8/2000 | Yimin | ............ | A61F 13/84 604/385.01 |
| 6,133,501 A * | 10/2000 | Hallock | ............ | A61F 13/495 604/369 |
| 6,135,988 A * | 10/2000 | Turner | ............ | A61F 13/49011 604/386 |
| 6,210,386 B1 * | 4/2001 | Inoue | ............ | A61F 13/49011 604/385.01 |
| 6,254,583 B1 * | 7/2001 | Coates | ............ | A61F 13/49004 604/385.14 |
| 6,264,639 B1 * | 7/2001 | Sauer | ............ | A61F 13/49011 604/385.101 |
| 6,383,170 B1 * | 5/2002 | Mishima | ............ | A61F 13/495 604/385.19 |
| 6,425,889 B1 * | 7/2002 | Kitaoka | ............ | A61F 13/49466 604/369 |
| 6,458,114 B1 * | 10/2002 | Mishima | ............ | A61F 13/49473 604/385.101 |
| 6,506,185 B1 * | 1/2003 | Sauer | ............ | A61F 13/49466 604/385.01 |
| 6,527,756 B1 * | 3/2003 | Mishima | ............ | A61F 13/49473 604/385.19 |
| 6,920,646 B2 * | 7/2005 | Crye | ............ | A41D 13/02 2/457 |
| 6,960,197 B1 * | 11/2005 | Gustafsson | ............ | A61F 13/495 604/348 |
| 7,001,368 B2 * | 2/2006 | Otsubo | ............ | A61F 13/5511 604/385.201 |
| 7,163,530 B1 * | 1/2007 | Toyoshima | ............ | A61F 13/4942 604/385.01 |
| 7,166,095 B1 * | 1/2007 | Coates | ............ | A61F 13/495 604/385.14 |
| 7,316,674 B2 * | 1/2008 | Infantino | ............ | A61F 13/49466 604/385.01 |
| 7,329,244 B2 * | 2/2008 | Otsubo | ............ | A61F 13/496 604/385.01 |
| 7,658,730 B2 * | 2/2010 | Conley | ............ | A61F 5/453 604/327 |
| 8,702,667 B1 * | 4/2014 | Johnson | ............ | A61F 13/471 604/349 |
| 8,951,239 B2 * | 2/2015 | Nakaoka | ............ | A61F 13/49011 604/385.16 |
| 9,498,393 B2 * | 11/2016 | Fukasawa | ............ | A61F 13/49011 |
| 2001/0016720 A1 * | 8/2001 | Otsubo | ............ | A61F 13/496 604/385.22 |
| 2002/0082570 A1 * | 6/2002 | Mishima | ............ | A61F 5/451 604/332 |
| 2002/0147438 A1 * | 10/2002 | Tanaka | ............ | A61F 13/49019 604/392 |
| 2002/0173763 A1 * | 11/2002 | Tsuji | ............ | A61F 13/4704 604/385.19 |
| 2003/0045853 A1 * | 3/2003 | Sauer | ............ | A61F 13/495 604/385.19 |
| 2003/0050616 A1 * | 3/2003 | Reynolds | ............ | A61F 13/49466 604/369 |
| 2004/0122404 A1 * | 6/2004 | Meyer | ............ | A61F 13/49012 604/385.19 |
| 2006/0206088 A1 * | 9/2006 | Lavon | ............ | A61F 13/15203 604/385.14 |
| 2007/0112322 A1 * | 5/2007 | Ashton | ............ | A61F 13/496 604/396 |
| 2007/0197984 A1 * | 8/2007 | Richardson | ............ | A61F 13/495 604/348 |
| 2007/0208316 A1 * | 9/2007 | Nakahata | ............ | A61F 13/15593 604/385.02 |
| 2007/0255245 A1 * | 11/2007 | Asp | ............ | A61F 13/495 604/385.19 |
| 2009/0043275 A1 * | 2/2009 | Perneborn | ............ | A61F 13/15756 604/391 |
| 2012/0191057 A1 * | 7/2012 | Takino | ............ | A61F 13/49011 604/385.29 |
| 2013/0041340 A1 * | 2/2013 | Kawakami | ............ | A61F 13/49009 604/385.29 |
| 2013/0123735 A1 * | 5/2013 | Ichikawa | ............ | A61F 13/49011 604/385.19 |

FOREIGN PATENT DOCUMENTS

| | | |
|---|---|---|
| JP | 2001-061888 A | 3/2001 |
| JP | 2001-252303 A | 9/2001 |

(56) References Cited

FOREIGN PATENT DOCUMENTS

| JP | 2012-239555 A | 12/2012 |
| JP | 2013-118962 A | 6/2013 |
| WO | 2013084915 A1 | 6/2013 |

OTHER PUBLICATIONS

Notification of Reason for Refusal for Japanese Patent Application No. 2014-202488, dated Sep. 28, 2015.

* cited by examiner

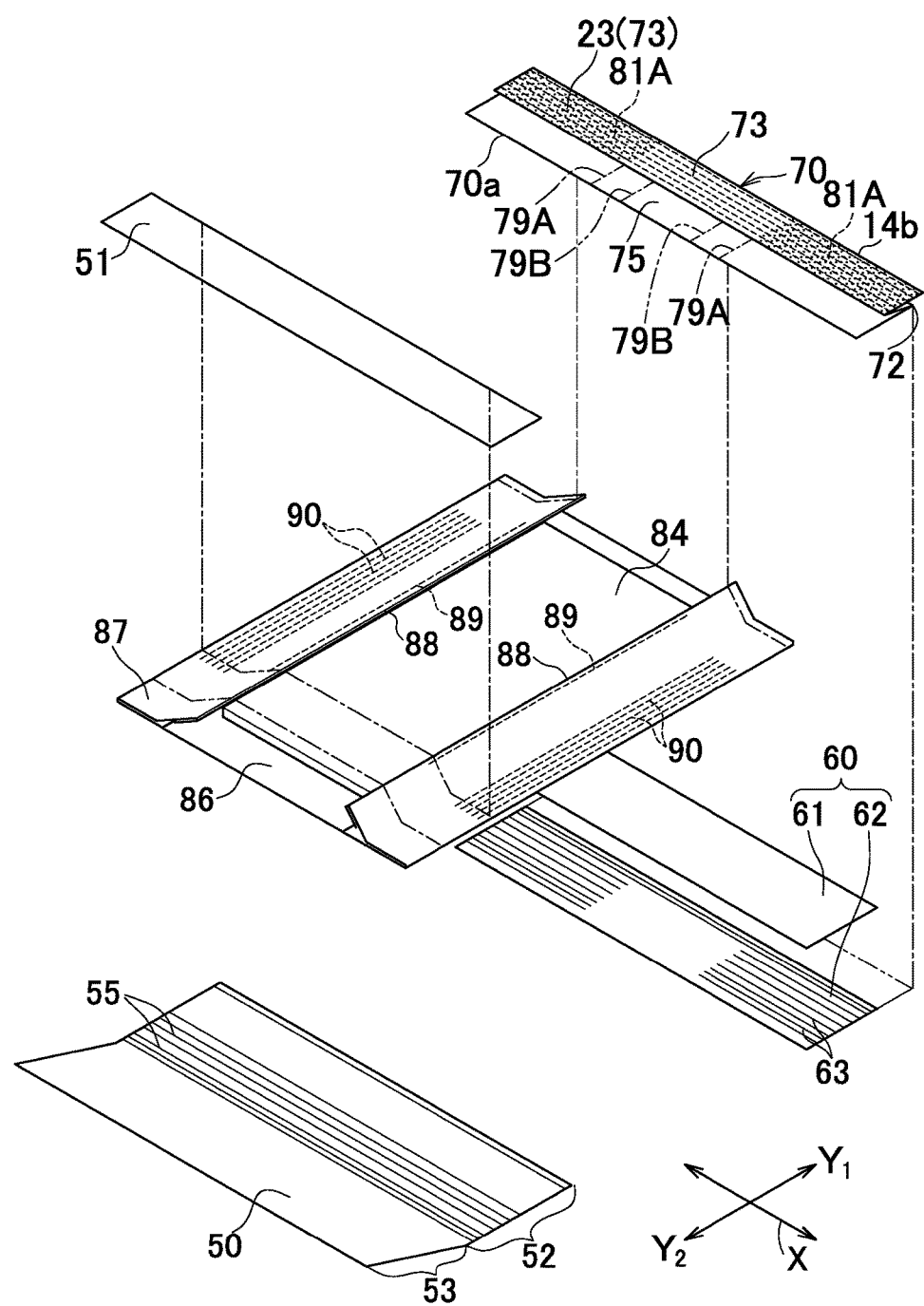

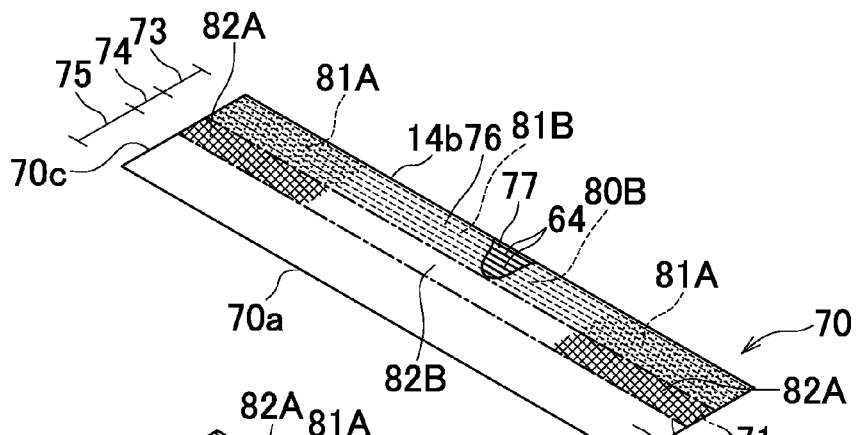
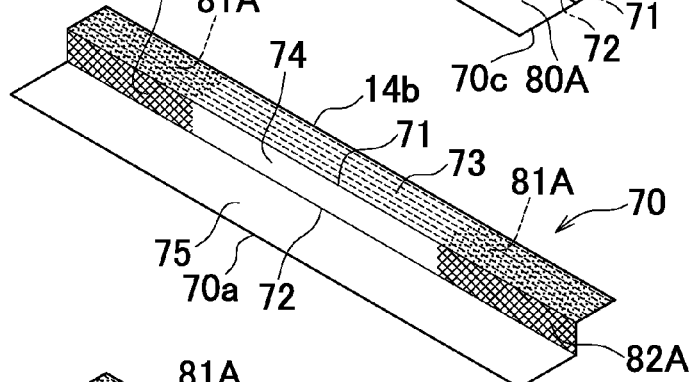
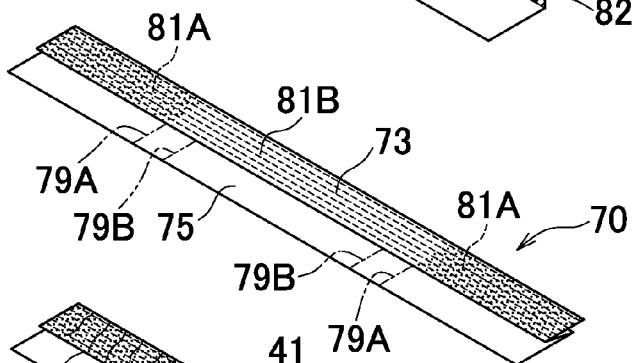
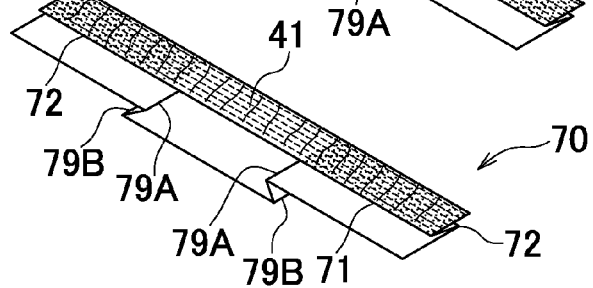

DISPOSABLE DIAPER

RELATED APPLICATIONS

The present application is a National Phase of International Application Number PCT/JP2015/070801, filed Jul. 22, 2015, which claims priority to Japanese Application Number 2014-202488, filed Sep. 30, 2014.

TECHNICAL FIELD

The present invention relates to disposable diapers.

BACKGROUND

Conventionally, disposable diapers are known providing with the pocket adapted to receive and retain body exudates is well known. For example, Patent Literature 1 discloses a disposable diaper having an absorbent structure arranged so as to center around a crotch region and elastic sheets extending in a transverse direction on the side of skin-facing surface of front and back waist regions so as to cover front and back edge portions of the absorbent structure wherein a pocket to receive body exudates is defined between the elastic sheets and the front and back edge portions of the absorbent structure.

CITATION LIST

Patent Literature

{PTL 1}: JP 2001-252303 A

SUMMARY

Technical Problem

In the disposable diaper according to the invention disclosed in the Patent Literature 1, the pocket defined in the front waist region and the back waist region is intended to receive and retain body exudates which flow from the crotch region toward the front and/or back regions.

However, with the diaper put on the wearer's body, the elastic sheets are stretched along with expansion of the front and back waist regions circumferentially around the wearer's waist. In consequence, the elastic sheets are put in close contact with the front and back edge portions of the absorbent structure which is, in turn, put in close contact with the wearer's body, resulting in a possibility that an opening of the receiving pocket defined between the respective elastic sheets and the respective front and back edge portions may be substantially closed and body exudates should not flow into the pocket but flow on the elastic sheets and soil the wearer's dorsal surface. If, to avoid such situation, a degree of fit at which the back waist region is put in contact with the wearer's body is attenuated, it will be facilitated to maintain the pocket in opened state but there is still another possibility that a gap may be formed between the wearer's body and the back waist region owing to the attenuated degree of fit and body exudates may flow not into the pocket but on the elastic sheet.

An object of the present invention is to improve the conventional diapers and to provide a disposable diaper including a pocket functioning to receive and retain body exudates flowing toward the waist-opening, restricting a possibility that the body exudates may adhere to the wearer's skin.

Solution to Problem

The present invention to solve the problem set forth above is directed to a disposable diaper having, in its state put on a wearer's body, an upward direction, a downward direction, a transverse direction and a front-back direction, and including a skin-facing surface, a non-skin-facing surface, a front waist region, a back waist region and a crotch region extending between the front and back waist regions.

The disposable diaper according to the present invention includes the features as described below:

the back waist region includes a belt region extending in the transverse direction on the skin-facing surface and a downwardly openable pocket located on the non-skin-facing surface and facing a central sub-region in the transverse direction of the belt region in the front-back direction. The pocket is defined by a pocket outside wall extending upward from a lower edge of the crotch region; a pocket inside wall facing the pocket outside wall and the belt region, respectively, in the front-back direction, and being continuous with the pocket outside wall through the folded portion extending in the transverse direction and extending downward from the folded portion so as to become continuous with the pocket inside wall; and in both lateral portions of the pocket inside and outside walls, both pocket lateral region tucked inward in the transverse direction by folding along a pair of folding lines facing each other in the transverse direction and extending in the upward and downward directions.

Advantageous Effects of Invention

The disposable diaper according to one or more embodiments of the present invention includes a pocket defined by pocket inside and outside walls and both pocket lateral portions formed by both lateral portions of these pocket inside and outside walls and arranged so as to be downward openable in the diaper put on the wearer's body. The pocket makes it possible to receive body exudates which would otherwise flow toward the back waist-opening, thereby preventing body exudates from leaking outward. In this way, it is possible for the diaper according to the present invention to avoid a discomfort feeling and skin troubles owing to contact of body exudates with the skin.

BRIEF DESCRIPTION OF DRAWINGS

FIG. 5 is a partially cutaway exploded perspective view of the diaper.

FIG. 6(a) is a partially cutaway developed plan view.

FIG. 6(b) is a diagram illustrating a step of folding a pocket base sheet.

FIG. 6(c) is a diagram illustrating a state in which the pocket base sheet has been folded along a first folding line and a second folding line.

FIG. 6(d) is a diagram illustrating a state in which the pocket base sheet has been folded along a third folding line.

DESCRIPTION OF EMBODIMENTS

A pull-on (i.e., pants-shaped) disposable diaper 10 illustrated as an example of disposable diapers according to the present invention has an upward direction Y1 and a downward direction Y2 (hereinafter may be referred to as "vertical direction"), a transverse direction X, a front-back direction Z, as viewed in the diaper 10 put on the wearer's body. Furthermore, the diaper 10 has a longitudinal axis P bisecting a dimension of the diaper 10 in the transverse direction X and a transverse axis Q bisecting a dimension of the diaper 10 in the vertical direction. The term "overlapped with each other in planar view" used in the present specification means that two or more elements overlap each other in the thickness direction.

Figure 1:
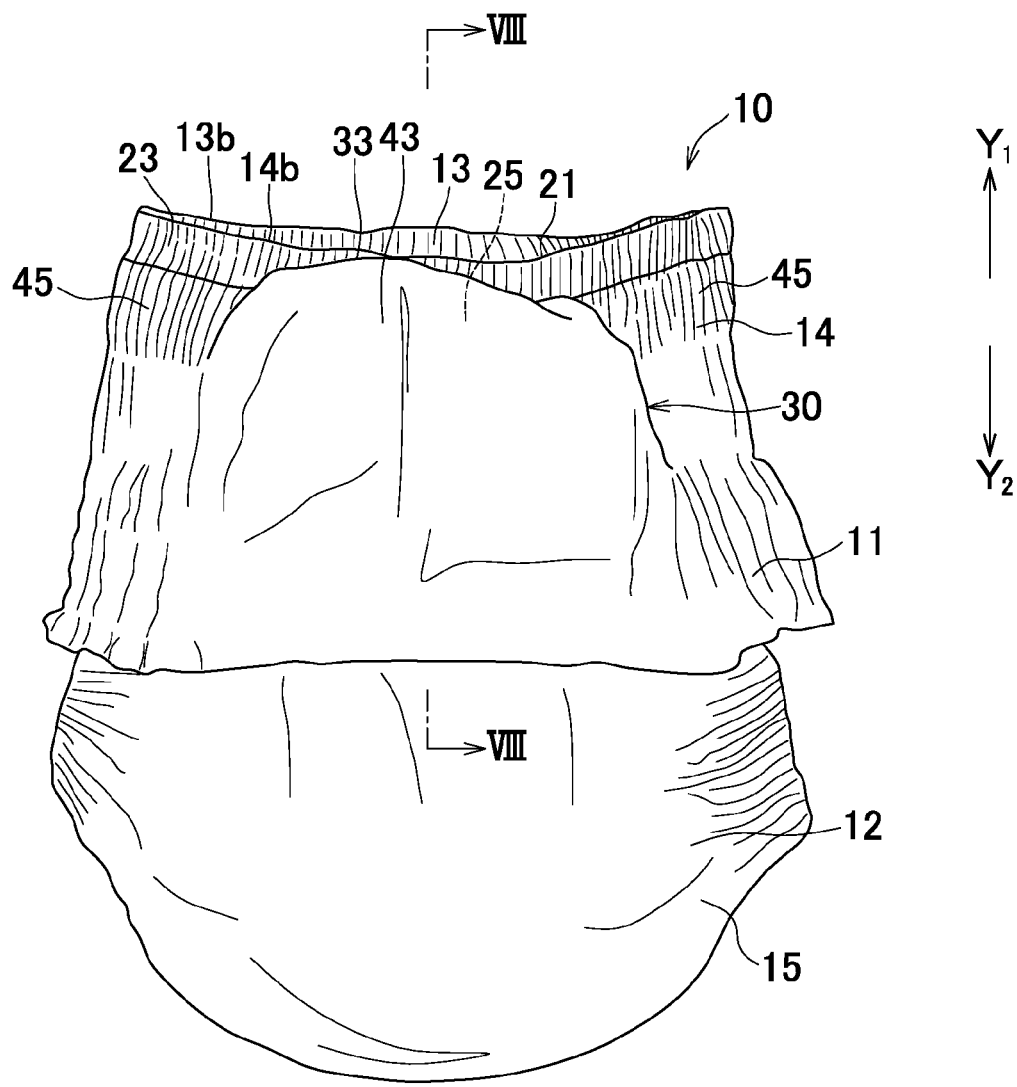
FIG. 1 is a back view of a disposable diaper according to the present invention.
Figure 4:
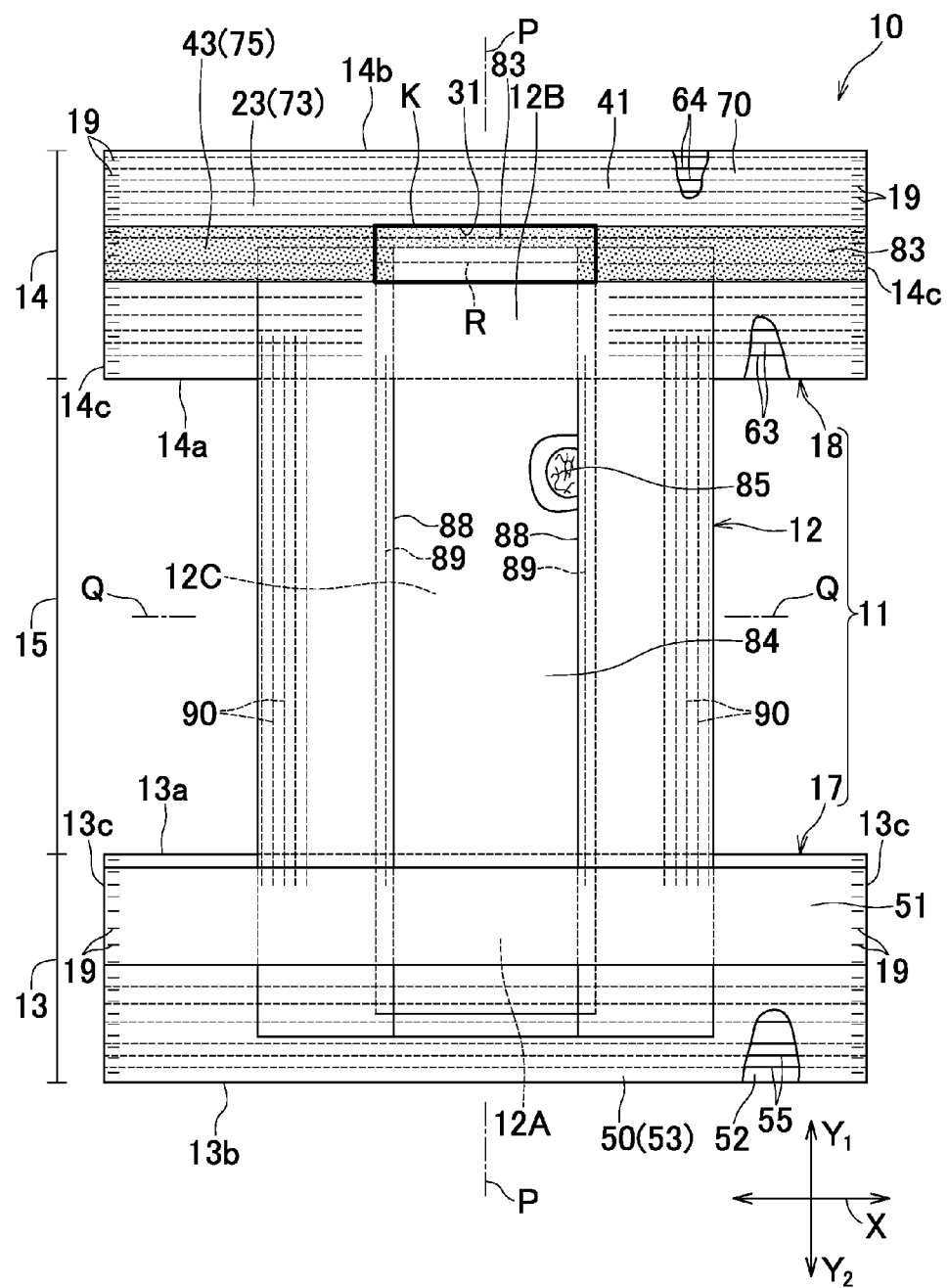
FIG. 4 is a partially cutaway developed view of the diaper in which respective elastic elements are under tension in up- and downward directions and a transverse direction of the diaper.

Referring to FIG. 1 and FIG. 4, the diaper 10 includes a skin-facing surface, a non-skin-facing surface opposite to the skin-facing surface, an elastic annular waist panel 11 circumferentially extending around the wearer's waist, an absorbent chassis 12 fixed to the elastic waist panel 11, a front waist region 13, a back waist region 14 and a crotch region 15 extending between the front and back waist regions 13, 14. The diaper 10 is formed symmetrically about the longitudinal axis P and the elastic waist panel 11 includes a front waist panel 17 lying in the front waist region 13 and a back waist panel 18 lying in the back waist region 14.

The front and back waist regions 13, 14 have transversely longer rectangular shapes respectively defined by inner edges 13a, 14a extending in the transverse direction X, outer edges 13b, 14b distanced from and opposite to each other in the vertical direction and extending in the transverse direction X and side edges 13c, 14c extending in the vertical direction between the inner and outer edges 13a, 13b; 14a, 14b. Both the side edges 13c of the front waist region 13 and both the side edges 14c of the back waist region 14 are respectively overlapped with each other and joined to each other at side seams 19 continually arranged in the vertical direction so as to define both side edge portions of the diaper 10 and to define a waist-opening 21 and a pair of leg-openings. The side seams 19 may be made by use of well known joining techniques, for example, various kinds of well known thermal welding techniques such as hot embossing/debossing and ultrasonic welding.

<Pocket>

Referring to FIG. 1 through FIG. 3 and FIGS. 7 and 8, the diaper 10 has a belt region 23 put in contact with the wearer's body on the side of the waist-opening 21 and a middle portion 41 of the belt region 23 wherein the middle portion 41 has an outer edge 41b and an inner edge 41a. Further, the diaper 10 has a pocket 30 located so as to face the belt region 23 in the front-back direction Z of the diaper 10 put on the wearer's body. The pocket 30 is formed centering on the longitudinal axis P over a given planar dimension region extending in the transverse direction X so that the pocket 30 may be opened downward (toward the crotch region when diaper 10 still not put on the wearer's body). The belt region 23 and the pocket 30 lie on the back waist region 14 adjacent to the waist-opening. The term "on the back waist region 14 adjacent to the waist-opening" used herein means a region extending from a line bisecting the dimension in the vertical direction of the back waist region 14 to the outer edge 14b.

The pocket 30 is defined by a pocket outside wall 43 facing the middle portion 41 in the front-back direction Z and extending upward from the vicinity the crotch region 15, a pocket inside wall 42 facing the pocket outside wall 43 and the belt region 23, respectively, in the front-back direction Z, and being continuous with the pocket outside wall 43 through a folded portion 33 and extending downward from the fold line 33 so as to become continuous with the pocket inside wall 42 of the middle portion 41 in the belt region 23, and both pocket lateral portions 32 formed from both the respective lateral portions of the inside and outside walls 42, 43 and tucked inward in the transverse direction X. The pocket inside wall 42 and the middle portion 41 of the belt region 23 are continuous with each other so that a folded portion 31 extending downward may be formed. The respective lateral portions of the pocket inside and outside walls 42, 43 are overlapped with each other to form both the pocket lateral portions 32 and both lateral portions 45 defined by regions other than both the pocket side portions 32 are attached to both the lateral portions of the belt region 23. Both the lateral portions 45 extend in the transverse direction X from the respective series of seams 19 and, in other words, the pocket 30 is not arranged to open in a range defined between the respective series of seams 19 but to open in the central sub-region of the back waist region 14. A size of the pocket opening is such as it is.

Figure 2:
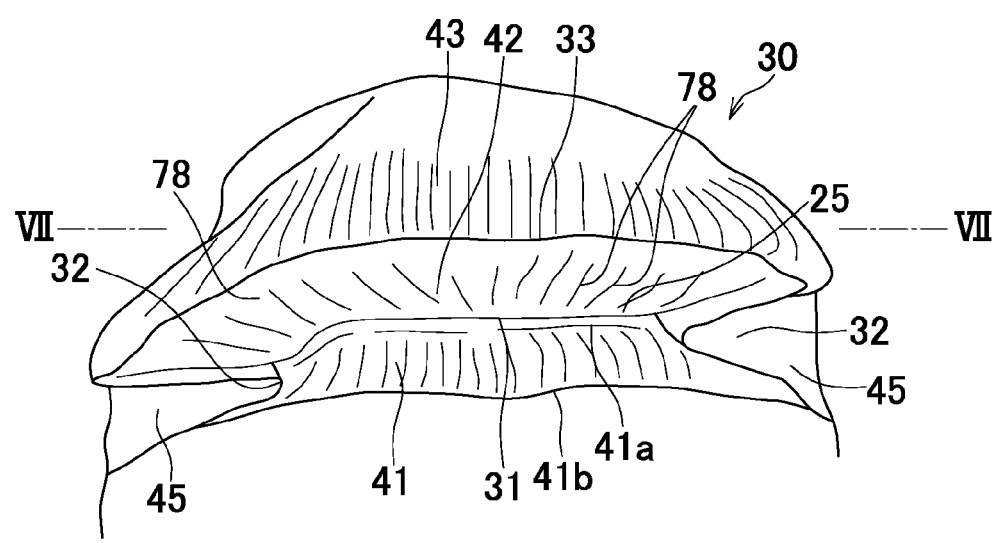
FIG. 2 is an overhead view of a back waist region in the diaper not put on the wearer's body.
Figure 3:
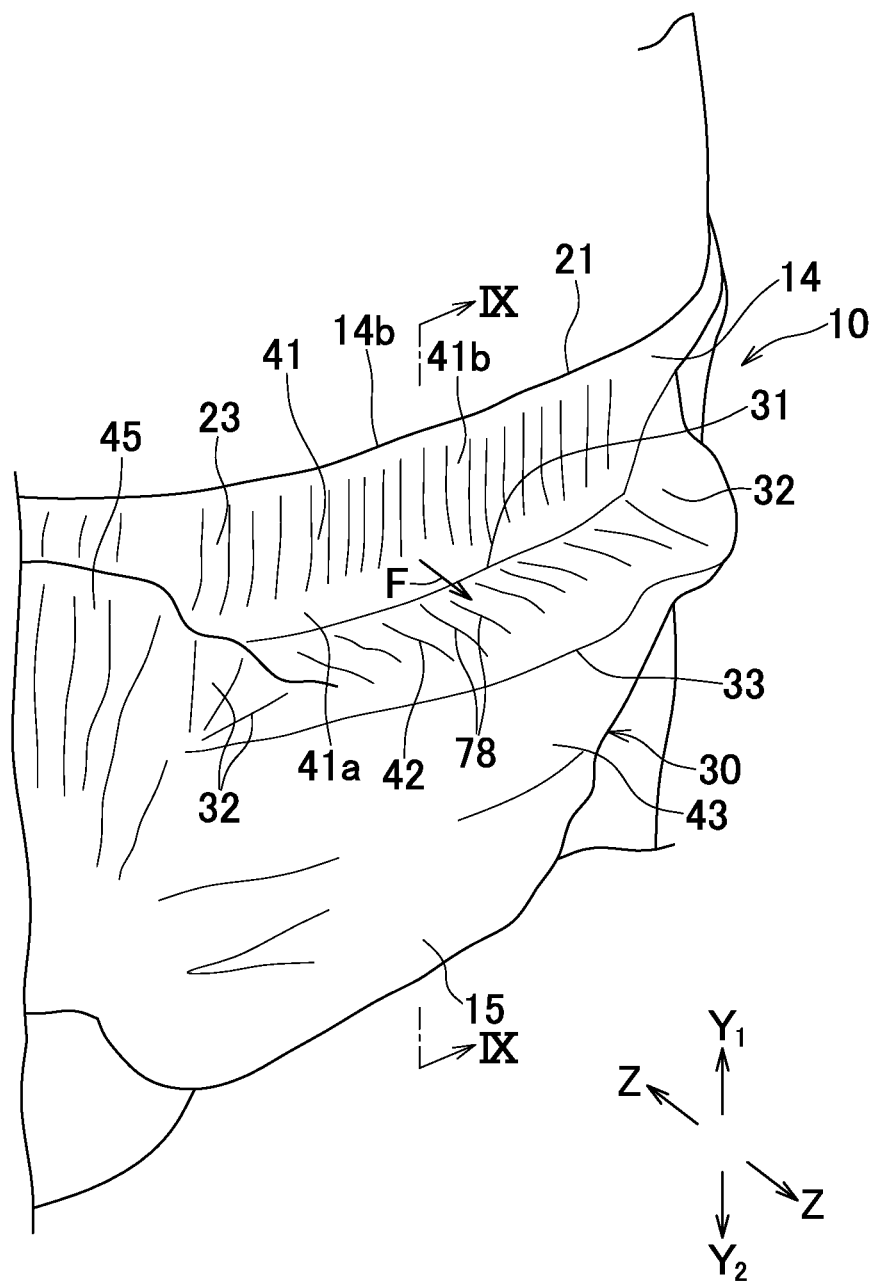
FIG. 3 is a perspective view of the back waist region in the diaper put on the wearer's body.

The pocket lateral portions 32 are tucked inward in the transverse direction X. Referring to FIG. 2, in a state that the folded portion 31 and both the pocket lateral portions 32 have been slightly developed in the diaper 10 is still not put on the wearer's body, a concave portion 25 opened upward is defined between the middle portion 41 and the pocket 30. A plurality of fold lines extending in the vertical direction inclusive of unintentionally folded lines may be formed without any problem as long as both the pocket lateral portions 32 are extensibly tucked.

Figure 8:
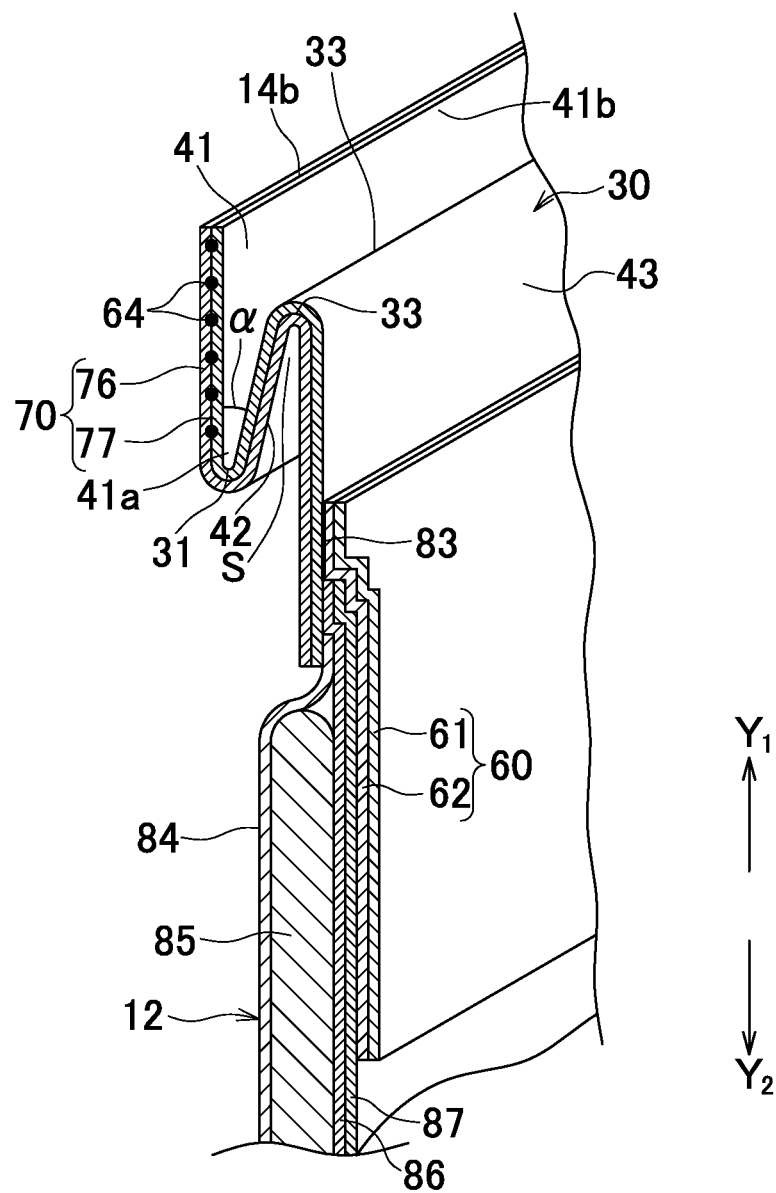
FIG. 8 is a schematic sectional view taken along line VIII-VIII in FIG. 1.
Figure 9:
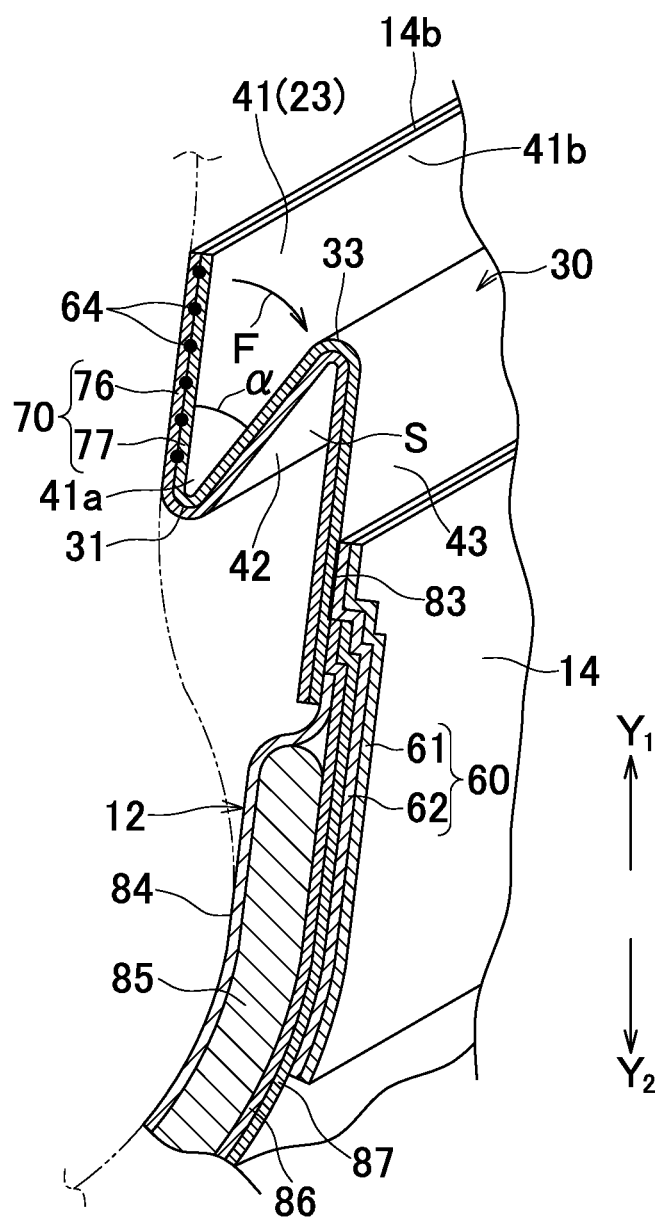
FIG. 9 is a schematic sectional view taken along line IX-IX in FIG. 3.

As above-described, the pocket 30 includes the folded portion 31 folded downward, both the pocket lateral portions 32 tucked inward in the transverse direction X and the folded portion 33 folded toward the waist-opening 21 (i.e., upward) wherein these portions and regions have been folded in the directions different from each other. Consequently, when the belt region 23 is stretched circumferentially around the wearer's waist, both the pocket lateral portions 32 stand up and the pocket inside wall 42 moves backward apart from the middle portion 41 of the belt region 23 (See FIG. 3). Referring to FIGS. 8 and 9, the pocket inside wall 42 extends at an angle of inclination relative to the middle portion 41 and this angle of inclination relative to the middle portion 41 becomes greater as the pocket inside wall 42 moves backward. In consequence, the pocket inside wall 42 gradually collapses as the angle of inclination as widens so that the pocket inside wall 42 may function as a top panel of the pocket 30 until the pocket 30 may have a container-like shape having a pocket space (containing space) S having a capability for receiving and containing a relatively large amount of body exudates therein.

<Elastic Waist Panel>

Referring to FIG. 4 and FIG. 5, the front waist panel 17 includes a front waist sheet 50 defining an outer shape of the front waist region 13. The front waist sheet 50 has a main region 52 in which a front edge portion 12A of the absorbent chassis 12 is located and an extending portion 53 located outside in the vertical direction of the main region 52. The extending region 53 is folded inward in the vertical direction along a fold line extending in the transverse direction X and fixed to the main region 52 and to the front edge portion 12A of the absorbent chassis 12 located on the interior surface of the main region 52. Between the main region 52 and the extending portion 53 of the front waist sheet 50, a plurality of string- or strand-like front waist elastic elements 55 are contractibly interposed under tension.

A front elastic sheet 51 which is extensible/contractible in the transverse direction X is arranged on a region of the front waist sheet 50 closer to the crotch region 15 than to the front waist elastic elements 55. The front elastic sheet 51 lies on the side of the skin-facing surface, partially covers the front edge portion 12A of the absorbent chassis 12 and fixed to this front edge portion 12A and to the portions of the main region 52 defined on both lateral sides thereof. The front elastic sheet 51 is formed of fibrous nonwoven fabrics made from elastomer fibers. Compared to the front elastic sheet made from inelastic fibrous nonwoven fabrics, the front elastic sheet 51 made from extensible/contractible fibrous nonwoven fabrics is superior to the former in texture and wear comfort. Though not illustrated, it is possible to arrange a back elastic sheet formed of extensible/contractible fibrous nonwoven fabrics on the skin-facing surface of the belt region 23 in the back waist region 14 so that the texture may be improved in the back waist region 14 also and the wear comfort of the diaper 10 as a whole maybe improved.

The back waist panel 18 includes a back waist sheet 60 composed of an interior sheet 61 defining the skin-facing surface and an exterior sheet 62 defining the non-skin-facing surface and a plurality of string- or strand-like back lower waist elastic elements 63 extending in the transverse direction X and contractibly fixed under tension between the interior and exterior sheets 61, 62. In the back waist region 14, there is provided a pocket base sheet 70 folded back on itself so as to have a generally W-like cross-section at the outer edges of the back waist panel 18.

<Pocket Base Sheet>

Referring to FIGS. 5 and 6 (a), the pocket base sheet 70 has a transversely longer rectangular shape defined by an inner edge 70a and an outer edge (corresponding to the back waist opening periphery 14b) both extending in the transverse direction X and both lateral edges 70c extending in the vertical direction between the inner and outer edges 14b, 70a and has a first surface 80A (corresponding to the skin-facing surface), a second surface 80B (corresponding to the non-skin-facing surface), and a first fold line 71 and a second fold line 72 extending in the transversely direction X parallel to each other. The pocket base sheet 70 has an outer edge portion 73 defined between the outer edge 14b and the first fold line 71, an intermediate portion 74 defined between the first fold line 71 and the second fold line 72 and an inner edge portion 75 defined between the second fold line 72 and the inner edge 70a. On the side of the second surface 80B of the outer edge portion 73, a pair of first joining regions 81A facing each other in the transverse direction X and, between these first joining regions 81A, a first non-joining region 81B is defined between these first joining regions 81A. On the side of the first surface 80A of the intermediate portion 74, a pair of second joining regions 82A face each other in the transverse direction X and, between these second joining regions 82A, a second non-joining region 82B is defined.

The pocket base sheet 70 further includes an interior sheet 76 defining the skin-facing surface, an exterior sheet 77 defining the non-skin-facing surface and a plurality of string- or strand-like back upper waist elastic elements 64 extending in the transverse direction X contractibly secured under tension between the interior and exterior sheets 76, 77. Referring to FIGS. 6(b), 6(c), the pocket base sheet 70 is folded along the first fold line 71 so that the second surface 80B side of the outer edge portion 73 and the second surface 80B side of the intermediate portion 74 may be put in contact with each other and folded along the second fold line 72 so that the first surface 80A side of the intermediate portion 74 and the first surface 80A of the inner edge portion 75 may be put in contact with each other. In this way, a state folded in a generally Z-shape as viewed in cross-section is maintained.

The first joining region 81A and the second joining region 82A respectively have dimensions in the transverse direction X which are approximately the same to each other and respective dimensions in the transverse direction X of the non-joining regions 81B, 82B defined between the two joining regions 81A, 82A are also approximately the same to each other. In a planar view of the diaper 10, the first and second non-joining regions 81B, 82B overlapped with each other. The first and second joining regions 81A, 82A are defined by, for example, joining means such as hot melt adhesive distributed on the respective regions or well known hot welding techniques such as heat sealing.

Referring to FIG. 6 (d), in the pocket base sheet 70, the outer edge portion 73 is contracted under a contractile force of the back upper waist elastic elements 64, folded along the first and second fold lines 71, 72 and joined to each other through the first and second joining regions 81A, 82A. Then the intermediate portion 74 and the inner edge portion 75 overlapped with each other are further folded along a pair of third fold lines 79A and a pair of fourth fold lines (mountain fold lines) 79B both extending in the vertical direction along the lateral edges of the second non-joining region 82A so that the portion except the outer edge portion 73 may have a generally W-shaped cross-section. A dimension in the transverse direction X of the pocket base sheet 70 folded in this manner is approximately the same as a dimension in the transverse direction X of the back waist region 14 in its natural state (i.e., a state in which the diaper is not worn).

Figure 7:
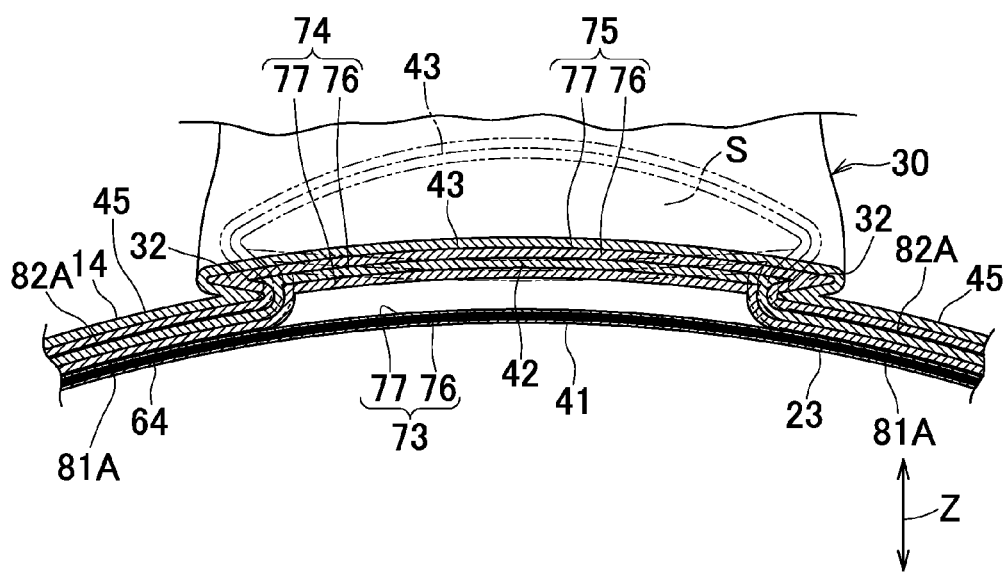
FIG. 7 is a schematic sectional view taken along line VII-VII in FIG. 2.

Referring to FIG. 4 and to FIGS. 7 through 9, the pocket base sheet 70 folded back on itself so as to form the generally W-shaped cross-section is fixed to the absorbent chassis 12 and to the back waist panel 18 through the joining regions (the third joining regions) 83 facing each other in the transverse direction X. As a result of folding the pocket base sheet 70 along a plurality of fold lines and fixing it in this state, the outer edge portion 73 defines the belt region 23 in the back waist region 14, the second non-joining region 82B in the intermediate portion 74 defines the pocket inside wall 42, and the portion of the inner edge portion 75 facing the second non-joining region 82B defines the pocket outside wall 43. Both the lateral portions of the pocket inside wall 42 and the pocket outside wall 43 are joined to each other in the state overlapping each other.

While the pocket base sheet 70 as a separately prepared pocket base sheet 70 is fixed to the back waist sheet 60 to form the pocket 30 and the other some elements according to the present embodiment, it is also possible to form the back waist sheet 60 and the pocket base sheet 70 from an integral sheet as long as the technical effect of the present invention is ensured. It is also possible to form the belt region 23 with use of the same sheet member as the back waist sheet 60 and to fix a separately prepared sheet element to the belt region 23, thereby forming the pocket 30. Further, it is also possible to form the pocket base sheet 70 from a single elastically extensible/contractible fibrous nonwoven fabrics or to interpose elastically extensible/contractible fibrous nonwoven fabrics instead of the back upper waist elastic elements 64 between the interior and exterior sheets 76, 77. In view of this, for example, the term "the pocket inside wall 42 is contiguous to the inner edge portion 41a of the middle portion 41 in the belt region 23" used herein means two cases, i.e., a case in which the middle portion 41 and the pocket inside wall 42 are formed of one and the same sheet element and folded in the folded portion 31 and a case in which the middle portion 41 and the pocket inside wall 42 are formed of separately prepared sheet elements and connected to each other in the folded portion 31. Furthermore, it is also possible to extend a dimension of the sheet element forming the absorbent chassis 12 backward and to fold the back waist panel together with the portion extending outward beyond the back waist panel, thereby forming the pocket 30.

<Absorbent Chassis>

Referring to FIG. 4, FIG. 5 and FIG. 8, the absorbent chassis 12 has a rectangular shape and includes the front edge portion 12A, a back edge portion 12B and an intermediate portion 12C defined between the front and back edge portions 12A, 12B. The absorbent chassis 12 is located on the side of the skin-facing surface and includes a liquid-permeable body side liner 84 made of fibrous nonwoven fabrics, a liquid-absorbent body 85, a leakage-barrier sheet 86 formed of liquid-impermeable plastic films and configured to cover an entire bottom surface of the absorbent body 85 and a liquid-impermeable or hardly-liquid-permeable cover sheet 87. The absorbent body 85 is composed of core materials including of wood fluff pulp and superabsorbent polymer particles and liquid-diffusible core wrapping sheets made of, for example, tissue paper to wrap the core materials as a whole.

The wrapping sheet 87 has both lateral portions lying outside both the lateral edges of the leakage-barrier sheet 86 as viewed in the transverse direction X. These lateral portions are folded inward (toward the side of the absorbent body 85) along fold lines extending adjacent both the lateral edges of the leakage-barrier sheet 86 in the vertical direction and fixed to the body side liner 84. Both the lateral portions include both edge portions fixed to the body side liner 84 and distanced from each other in the vertical direction, proximal edge portions fixed to both the lateral portions of the body side liner 84 and distal edge portions 88 extending in the vertical direction between both the edge portions and extending in the vertical direction in parallel to the proximal edge portions. In each of the distal edge portions 88, the outer edge portion of the wrapping sheet 87 is folded and fixed to form a sleeve-like portion and a plurality of string- or strand-like cuff elastic elements 89 extending in the vertical direction are contractibly attached under tension to the inner side of the sleeve-like portion. Under contraction of the cuff elastic elements 89, the respective outer edge portions are spaced away from the body side liner 84 toward the wearer's body so as to form the barrier cuffs adapted to be kept in close contact with the wearer's thighs, thereby preventing body exudates from leaking. Both the lateral portions of the wrapping sheet 87 are also provided with a plurality of string- or strand-like leg elastic elements 90 extending in the vertical direction and contractibly attached thereto under tension.

The leg elastic elements 90 are composed of a plurality of elastic elements at given intervals in the transverse direction X so as to form an elastic portion planarly kept in close contact with the wearer's thighs at a degree of fit, thereby preventing effectively body exudates from leaking out sideways. With the diaper put on the wearer's body, the back edge portions of the leg elastic elements 90 overlap the back lower waist elastic elements 63 in the back waist region 14 in planar view. The leg elastic regions under the contractile force of the leg elastic elements 90 and the waist elastic region under the contractile force of the back lower waist elastic elements 63 are overlapped with each other in planar view to define an imaginary elastic portion surrounding the thighs of the wearer.

Referring to FIG. 4, the respective both lateral portions 45 of the pocket inside and outside walls 42, 43 are fixed through the joining region 83 having a concave portion opening toward the transverse axis Q to the belt region 23 and the back edge portion 12B of the absorbent chassis 12 but not fixed to the back edge portion 12B of the absorbent chassis 12 in the portion of the wrapping sheet 87 defined between a pair of the distal edge portions 88. The pattern of joining regions arranged for the pocket base sheet 70 defines, between the non-joining region thereof and the back edge portion 12B of the absorbent chassis 12, a back space R adapted to receive and to retain body exudates having flowed to the back waist region 14.

Generally, relatively few months old baby loose fecal exudates in various situations, for example, during breast-feeding or in a posture of being lifted up in a mother's arms and, in consequence, loose fecal exudates may leak from the back waist-opening and/or loose fecal exudates may be pressed against and soil the wearer's back. In addition, a space to receive body exudates may be formed between the diaper and the wearer's body when the waist-opening of the diaper put on the wearer's body slips down in the front waist region. However, the buttocks have an external form protruding backward and such an undesired gap will be hardly formed. To assure that body exudates are received and temporarily retained, a pocket space S having a 3D configuration in the diaper 10 put on the wearer's body should be intentionally arranged.

To solve such problems, various arrangements, for example, the arrangement such that the front and back waist regions and/or the crotch region is provided with the reception space extending downward or backward has been disclosed. However, the diaper 10 provided with the pocket 30 arranged so that, on the back side, the pocket 30 opens downward (i.e., toward the transverse axis Q) and then extends upward is not known.

According to the present embodiment, the belt region 23 and the pocket 30 are located on the waist-opening in the back waist region 14 and the belt region 23 is put in close contact with the wearer's body under tensile stress of the back upper waist elastic elements 64. Consequently, body exudates flowing from the crotch region 15 toward the back waist-opening is prevented from leaking out and the body exudates of which further flow was inhibited into the pocket space S convexly extending upward and is received therein to be temporarily contained therein. The inhibited body exudates are guided into the pocket 30 defined on the back waist region 14, whereby prevented are a discomfort feeling and various skin troubles owing to the body exudates which may otherwise come in contact with the wearer's skin. The pocket 30 is not influenced by extension/contraction of the belt region 23 and, therefore, the pocket opening should not be closed even when the back waist region 14 is stretched.

Further, the pocket 30 is located above the upper edge portion (i.e., back edge portion) of the absorbent body 85 and it is possible for the pocket 30 to receive the body exudates which has not been absorbed by the absorbent body and flows toward the back waist opening.

The pocket base sheet 70 to form the pocket 30 is partially joined through the joining region 83 extending inward in the transverse direction X from the side seams 19 to the back waist region 14 and the pocket base sheet 70 itself is located outboard of the leg elastic elements 90 and the cuff elastic elements in the vertical direction without overlapping with them in planar view of the diaper 10. For this reason, even if the contractile force of the leg elastic elements 90 and the cuff elastic elements 89 indirectly act on the pocket outside wall 43 so as to pull them downward, it is not possible that the pocket outside wall 43 may be pulled downward, whereby the folded portion 33 may collapse and the pocket space S may disappear.

Referring again to FIG. 2, FIG. 3 and FIG. 7, in the diaper 10 not put on the wearer's body, both the pocket lateral portions 32 of the pocket 30 are still in a state that these portions 32 are tucked in toward the longitudinal axis P so as to have a generally V-shaped cross-sections, respectively, and, in the diaper 10 put on the wearer's body, both the pocket lateral portions 32 stand up and the pocket inside wall 42 is apart from the middle portion of the belt region 23 to form the space S. In the diaper 10 not put on the wearer's body, both the pocket lateral portions 23 are in folded back state and the middle portion 41 of the belt region 23 is kept in contact with the pocket inside wall 42. In consequence, the back waist region 14 as a whole is made further compact and the dimension in the thickness direction Z is reduced compared to the diaper 10 put on the wearer's body. For this reason, the diaper 10 according to the present embodiment is superior in aptitude for storage and for transportation.

Also when the wearer is in a spine posture and the pocket 30 is under a wearer's body weight, there is no possibility that the pocket base sheet 70 may be deformed under the body weight and may create a foreign-body feeling against the wearer owing to partial thickness change in the back waist region 14. This is for the reason that, even when the pocket 30 is under the wearer's body weight, the pocket lateral portions 32 are in folded states and the middle portion 41 of the belt region 23 and the pocket inside wall 42 are kept in contact with each other. Both the pocket lateral portions 32 are arranged to flex/extend in a direction in which both the pocket lateral portions 32 move closer to or draw apart from the wearer's body, i.e., in the front-back direction Z and, therefore, upon being freed from the body weight, both the pocket lateral portions 32 stand up in a direction F (see FIG. 9) in which both the pocket lateral portions 32 are disengaged from the wearer's body and the 3D pocket space S is formed again.

With the arrangement mentioned above, even when the baby is lifted up in a mother's arms in a state that the baby's back is hugged by a mother's arms and the pocket 30 is subjected to the force repetitively pressing the pocket 30 against the baby's body, the flexing/extending movement of both the pocket lateral portions 32 makes it possible for the pocket 30 to regain the 3D configuration stably and repetitively. Consequently, even when the diaper is put on a relatively few month old baby generally apt to change his or her posture at short intervals and to repeat loose fecal exudates frequently, it is ensured to receive loose fecal exudates in the pocket space S. Further, according to the present embodiment, the pocket inside wall 42 has the desired dimension in the vertical direction as has been described above and moves backward at an angle relative to the middle portion 41 as both the pocket lateral portions 32 stand up and the pocket inside wall 42 functions as the top panel for of the pocket 30. In this way, it is possible for the pocket 30 according to the present embodiment to receive and to retain a larger quantity of body exudates in comparison with the pocket having neither the top panel nor the folded structure.

In the diaper 10 put on the wearer's body, when the belt region 23 is stretched in the transverse direction X (i.e., circumferential direction around the waist) until the gathers formed under contractile force of the back upper waist elastic elements 64 disappear, the tucking effect in both the pocket lateral portions 32 should not be released and the pocket inside wall 42 may move toward the middle portion 41 until the pocket space S may disappear. In view of such apprehension, a degree of contraction in the transverse direction X of the belt region 23 inclusive of the middle portion 41 (i.e., a length dimension in the transverse direction X of a contracting portion) is preferably larger than a contraction degree in the transverse direction X of the pocket inside wall 42 and/or the pocket outside wall 43 to assure that the pocket 30 maintains 3D configuration even when the belt region 23 is stretched in the transverse direction X. As long as such necessary condition is satisfied, it is assured that both the pocket lateral portions 32 never completely collapse and the pocket 30 maintains its 3D configuration even when the belt region 23 is stretched in the transverse direction X at a given ratio relative to the natural state (i.e., the contracted state) thereof.

In view of this, preferably, the belt region 23 is provided with the elastic elements which are extensible/contractible in the transverse direction X but the pocket inside wall 42 and/or the pocket outside wall 43 are not provided with the elastic elements. In other words, the latters are preferably arranged so as to be substantially not elastically extensible/contractible. Though not illustrated, if the pocket inside wall 42 and/or the pocket outside wall 43 are also provided with elastic elements extensible/contractible in the transverse direction X, these elastic elements preferably have a contraction degree lower than that of the elastic elements arranged in the middle portion 41, i.e., the back upper waist elastic elements 64. If the pocket inside wall 42 is provided with the elastic elements merely extensible but not contractible in the transverse direction X, even when the middle portion 41 is stretched and, in consequence, a force which would otherwise collapse both the pocket lateral portions 32 is generated, the above-mentioned elastic elements arranged in the pocket inside wall 42 will resist such force to maintain both the pocket lateral portions 32 standing up and to maintain the pocket inside wall 42 distanced from the middle portion 41. In this way, it is possible for the pocket 30 to maintain its 3D configuration more stably. When both the pocket inside wall 42 and the pocket outside wall 43 are elastically extensible/contractible, a contraction degree in the transverse direction of the pocket inside wall 42 is preferably higher than a contraction degree in the transverse direction X of the pocket outside wall 43.

<Measuring Method for Contraction Percentage of Respective Regions>

In the developed diaper 10, test pieces each having a given size (for example, longitudinal dimension of 15 mm×transverse dimension of 100 mm) were cut out from a layered region of the pocket outside wall 43 and the belt region 23 (i.e., region surrounded by a thick frame K) and dimensions of the respective test pieces were measured by the following steps as described below: i) One of both edge portions facing each other in the transverse direction X of the test piece is held; ii) Clip and weight are attached to the other edge portion and the test piece is suspended vertically to floor surface so that the test piece may be in a state without any crinkle. In such a state, two positions facing and distanced from each other in the transverse direction X in a region including elastic elements therein (if none of the elastic elements is present, a given region of sheet) are marked with, for example, ink. A distance between these two marks is measured as a dimension (L1) of the test piece in its contractile state. Heft of the weight may be appropriately adjusted as long as the weight does not act to stretch the elastic element arranged in the test piece; and iii) The clip and the weight are removed from the test piece and the test piece is stretched in the transverse direction X until gathers having been generated under contraction of the elastic element disappear. Then, a distance dimension between two marks is measured as a dimension (L2) of the test piece in its stretched state. From these dimensions L1, L2 measured by the method as described above, contraction percentages (%) of the respective test pieces were calculated according to a formula of contraction percentage=((L2−L1)/L2)×100 (%).

According to the present embodiment, the leakage-barrier sheet 86 extends from the upper edge portion (i.e., back edge portion) toward the folded portion 33 and has a dimension in the transverse direction X larger than the dimension in the transverse direction X of the opening of the pocket 30. In this manner, it is possible for the leakage-barrier sheet 86 dimensioned to be wider than the opening of the pocket and located adjacent to the opening of the pocket 30 to prevent body exudates flowing into the pocket space S from leaching out.

Referring again to FIG. 3, the upper edge portion (i.e., outer edge portion) of the belt region 23 lies above the folded portion 33 of the pocket 30. In consequence, there is unlikely that body exudates may leak through the waist-opening since the pocket 30 is maintained in opened state and the belt region 23 is kept in close contact with the wearer's body. In addition, the middle portion 41 is constituted by the pocket 30 and the pocket base sheet 70 and the dimensions in the transverse direction X of these constituent sheet members are same to each other. For this reason, the dimension in the transverse direction X of the pocket inside wall 42 which is continuous with the inner edge portion 41*a* of the middle portion 41 is contracted under contraction of the back upper waist elastic elements 64 even when the pocket inside wall 42 is provided with none of elastic elements. Thereby the pocket inside wall 42 is formed with a plurality of gathers (or ridges) extending in the vertical direction. These gathers extending in the vertical direction function like ribs to improve stiffness in the transverse direction X as well as in the vertical direction of the pocket inside wall 42. Consequently, the pocket 30 having both the pocket lateral portions 32 in stand-up posture makes it possible for the pocket 30 to keep the stable container-like 3D configuration. Though not illustrated, also in the front waist region 13, it is possible to arrange a pocket configured to open downward in a manner similar to the pocket 30 arranged in the back waist region 14.

Alternative Embodiment 1

Figure 10:
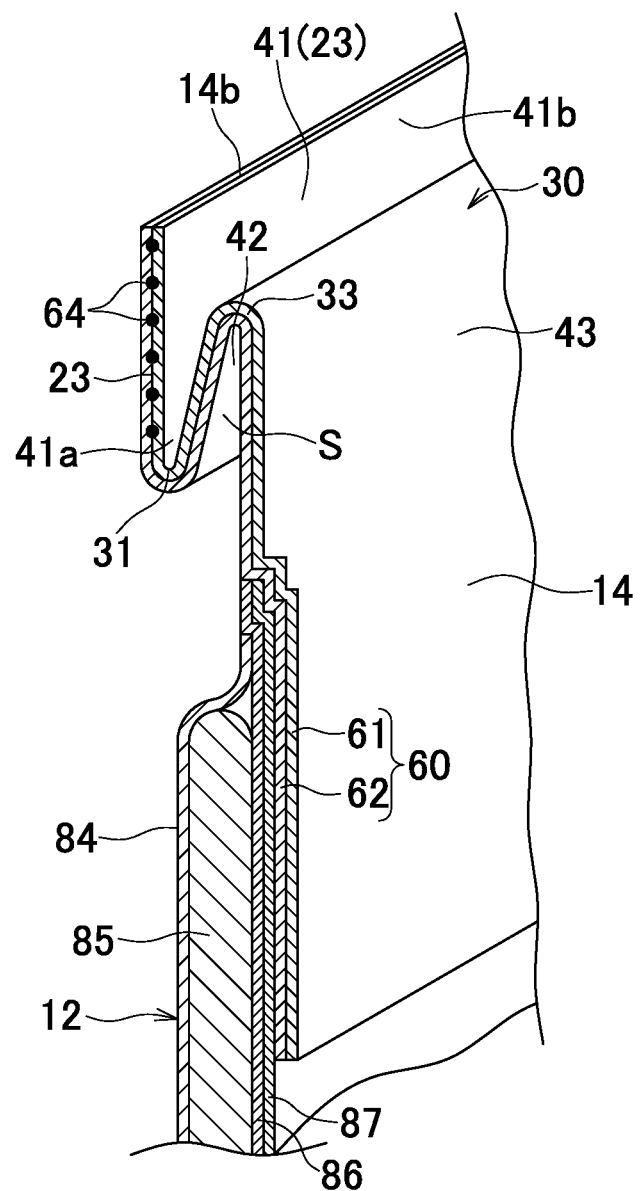
FIG. 10 is a sectional view similar to FIG. 8, illustrating an alternative embodiment 1.

Referring to FIG. 10, according to the present alternative embodiment, the constituents such as the belt region 23 and the pocket 30 are formed from the back waist sheet 60. Specifically, the back waist sheet 60 extends upward beyond the back edge portion 12B of the absorbent chassis 12 and these protruding portions of the back waist sheet 60 are folded so as to form both the lateral portions 32 and the folded portions 31, 33 and then joined together through joining regions corresponding to the first and second joining regions 81A, 82A. Also in the diaper 10 arranged in such manner, the pocket 30 is configured to open downward and to move to or from the belt region 23 and whereby the technical effects of the present invention is achieved.

Alternative Embodiment 2

Figure 11:
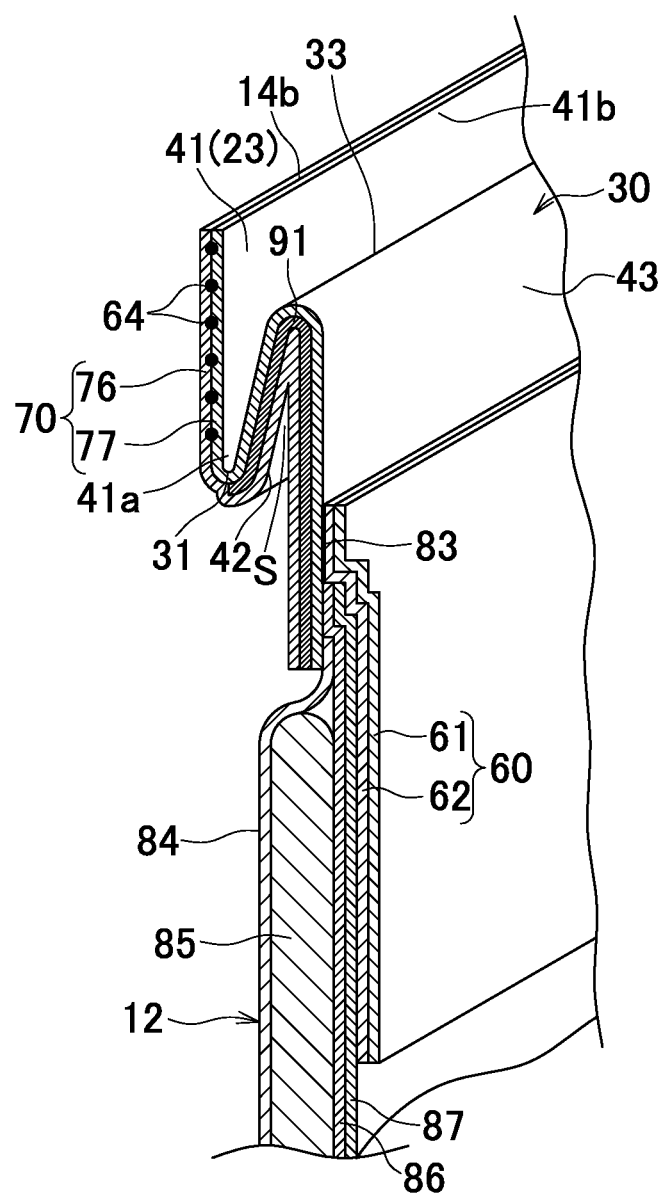
FIG. 11 is a sectional view similar to FIG. 8, illustrating an alternative embodiment 2.

Referring to FIG. 11, according to the present alternative embodiment, the impermeable sheet 91 is located between the interior and exterior sheets 76, 77 of the pocket base sheet 70. The impermeable sheet 91 is preferably formed of air-permeable fibrous nonwoven fabrics or plastic films and extends from the pocket outside wall 43 to the folded portion 33 and further from the folded portion 33 to the pocket inside wall 42. It is impossible for the pocket base sheet 70 alone which is formed of fibrous nonwoven fabrics to retain loose fecal exudates having high flow ability and such loose fecal exudates may leach out to the exterior surface of the pocket base sheet. However, the impermeable sheet 91 makes it possible to improve the leakage-barrier effect and to prevent the loose fecal exudates from leaching out. The impermeable sheet 91 preferably has a dimension in the transverse direction X larger than the dimension in the transverse direction X of the opening of the pocket 30 from the standpoint of further effectively preventing body exudates from leaching out. While the impermeable sheet 91 is prepared separately from the leakage-barrier sheet 86 according to the present alternative embodiment, it is possible to arrange so that the leakage-barrier sheet 86 extends into the pocket 30.

The constituent materials of the diaper 10 according to the present invention are not limited to those described in the specification but the other various types of material widely used in the relevant technical field may be used without limitation unless otherwise stated.

While a structure in which the front and back waist regions 13, 14 are formed from the front and back waist panels 17, 18 prepared separately from each other is exemplarily described as a basic structure of the diaper 10 in the present specification, it is also possible to form the front and back waist regions 13, 14 and the crotch region 15 from a continuous panel. Further, the basic structure of the diaper 10 according to the present invention is not limited to the pull-on type in which the front and back waist regions 13, 14 are previously joined to each other along the respective both lateral edge portions and it is possible to implement the present invention in a form of so-called open-type diaper in which the respective both lateral edge portions are connected through tape fasteners.

The terms "first", "second" and "third" used in the specification and Claims are used merely to distinguish the similar elements, similar positions or other similar items.

The disclosure relating to the present invention described hereinabove may be arranged at least as follows:

A disposable diaper having, in its state put on a wearer's body, an upward direction, a downward direction, a transverse direction and a front-back direction, and including a skin-facing surface, a non-skin-facing surface, a front waist region, a back waist region and a crotch region extending between the front and back waist regions, wherein:

the back waist region includes a belt region extending in the transverse direction on the skin-facing surface and a downwardly openable pocket located on the non-skin-facing surface and facing a central sub-region in the transverse direction of the belt region in the front-back direction;

the pocket is defined by a pocket outside wall extending upward from the side of the crotch region; a pocket inside wall facing the pocket outside wall and the belt region, respectively, in the front-back direction, and being continuous with the pocket outside wall through the folded portion extending in the transverse direction and extending downward from the folded portion so as to become continuous with the pocket inside wall; and in both lateral portions of the pocket inside and outside walls, both pocket lateral region tucked inward in the transverse direction by folding along a pair of folding lines facing each other in the transverse direction and extending in the upward and downward directions.

The disposable diaper according to the present invention disclosed in the above paragraph may include embodiments at least as described below and these embodiments may be taken in isolation or in combination with one another.

(1) The belt region and the pocket are located on the side of the waist-opening in the back waist region.

(2) The diaper further includes an absorbent body extending from the crotch region to the front and back waist regions wherein the pocket inside and outside walls are located above an upper end of the absorbent body.

(3) The belt region is extensible/contractible in the transverse direction.

(4) A contraction percentage of the belt region in the transverse direction is higher than respective contraction percentages of the pocket inside and outside walls in the transverse direction.

(5) The contraction percentage of the belt region in the transverse direction is higher than the contraction percentage of the pocket inside wall and the contraction of the pocket inside wall in the transverse direction is higher than the contraction percentage of the pocket outside wall in the transverse direction.

(6) The diaper further includes an impermeable sheet extending from an upper edge portion of the absorbent body to the folded portion and further extending from the folded portion toward a lower end of the pocket inside wall.

(7) The diaper further includes an impermeable sheet extending toward the folded portion and having a dimension in the transverse direction larger than a dimension in the transverse direction of an opening of the pocket.

(8) A waist-opening periphery in the back waist region is located above the folded portion.

The invention claimed is:

1. A disposable diaper, comprising:
in a state that the diaper is put on a wearer's body, an upward direction, a downward direction, a transverse direction, and a front-back direction, and
a skin-facing surface, a non-skin-facing surface, a front waist region, a back waist region, and a crotch region extending between the front and back waist regions,
wherein
the back waist region includes
a belt region extending in the transverse direction on the skin-facing surface and having a central region in the transverse direction, and
a downwardly openable pocket facing the central region of the belt region in the front-back direction;
the pocket is defined by
(i) a pocket outside wall extending upward from the crotch region and including a lateral portion;
(ii) a pocket inside wall facing the pocket outside wall and the belt region in the front-back direction and including a lateral portion, the pocket inside wall being continuous with the pocket outside wall through a folded portion extending in the transverse direction, and the pocket inside wall extending downward from the folded portion to become to be continuous with the belt region; and
(iii) the lateral portions of the pocket inside and outside walls,
the pocket has a pair of folding lines facing each other in the transverse direction, each of the folding lines extending in the upward and downward directions, and
each of the lateral portions of the pocket inside and outside walls is tucked inward in the transverse direction by being folded along the pair of folding lines.

2. The diaper according to claim 1, wherein the belt region and the pocket are located on a waist-opening side in the back waist region.

3. The diaper according to claim 1, further comprising an absorbent body extending from the crotch region to the front and back waist regions,
wherein the pocket inside and outside walls are located above an upper end of the absorbent body.

4. The diaper according to claim 3, further comprising a liquid-impermeable sheet extending from the upper end of the absorbent body to the folded portion and further extending from the folded portion along the pocket inside wall from an upper end of the pocket inside wall toward a lower end of the pocket inside wall.

5. The diaper according to claim 1, wherein the belt region is extensible/contractible in the transverse direction.

6. The diaper according to claim 1, wherein a contraction percentage of the belt region in the transverse direction is higher than respective contraction percentages of the pocket inside and outside walls in the transverse direction.

7. The diaper according to claim 1, wherein
a contraction percentage of the belt region in the transverse direction is higher than a contraction percentage of the pocket inside wall, and
the contraction percentage of the pocket inside wall in the transverse direction is higher than a contraction percentage of the pocket outside wall in the transverse direction.

8. The diaper according to claim 1, further comprising a liquid-impermeable sheet extending toward the folded portion and having a dimension in the transverse direction larger than a dimension of an opening of the pocket in the transverse direction.

9. The diaper according to claim 1, wherein a waist-opening periphery in the back waist region is located above the folded portion.

10. The diaper according to claim 1, wherein
the back waist region includes
the folded portion extending in the transverse direction and between the pocket inside wall and the pocket outside wall, and
a further folded portion extending in the transverse direction and between the belt region and the pocket inside wall.

11. The diaper according to claim 1, wherein the pocket inside wall is between the pocket outside wall and the belt region in the front-back direction.

12. The diaper according to claim 1, further comprising an absorbent body extending from the crotch region to the front and back waist regions, wherein an entirety of the pocket inside and outside walls is located above an upper end of the absorbent body.

* * * * *